United States Patent [19]

Fischer et al.

[11] Patent Number: 4,554,156

[45] Date of Patent: Nov. 19, 1985

[54] WOUND TREATING AGENT

[75] Inventors: Herbert Fischer, Burg; Botho Kickhöfen, Freiburg; Ekkehard Vaubel, West Berlin, all of Fed. Rep. of Germany

[73] Assignee: Max-Planck-Gesellschaft zur, Fed. Rep. of Germany

[21] Appl. No.: 674,366

[22] Filed: Nov. 26, 1984

Related U.S. Application Data

[63] Continuation of Ser. No. 561,126, Dec. 13, 1983, abandoned, which is a continuation of Ser. No. 304,479, Sep. 22, 1981, abandoned.

[30] Foreign Application Priority Data

Sep. 24, 1980 [DE] Fed. Rep. of Germany ....... 3036033

[51] Int. Cl.$^4$ .............................................. A61K 31/78
[52] U.S. Cl. ........................................ 424/81; 514/944
[58] Field of Search ........................... 424/81; 514/944

[56] References Cited

U.S. PATENT DOCUMENTS 3,618,213  11/1971  Shepherd et al. ..................... 424/81

FOREIGN PATENT DOCUMENTS 2725261  12/1978  Fed. Rep. of Germany .

*Primary Examiner*—Albert T. Meyers
*Assistant Examiner*—John W. Rollins
*Attorney, Agent, or Firm*—Bernard, Rothwell & Brown

[57] ABSTRACT

The present invention provides a wound treating agent in powder form based on a swellable organic polymer, which comprises a cross-linked polymer of a hydrophilic acrylic or methacrylic acid derivative, which polymer is permeated by a gellable polysaccharide and/or protein or polypeptide, the agent being obtainable by polymerizing a hydrophilic acrylic or methacrylic acid derivative in the presence of a dissolved, gellable polysaccharide and/or protein or polypeptide and of a cross-linking agent.

The present invention also provides a process for the production of this wound treating agent, wherein a hydrophilic acrylic or methacrylic acid derivative is polymerized in an aqueous solution of a gellable polysaccharide and/or protein or polypeptide in the presence of a cross-linking agent and of a conventional polymerization initiator, to give a transparent gel which is dried and pulverized.

21 Claims, 1 Drawing Figure

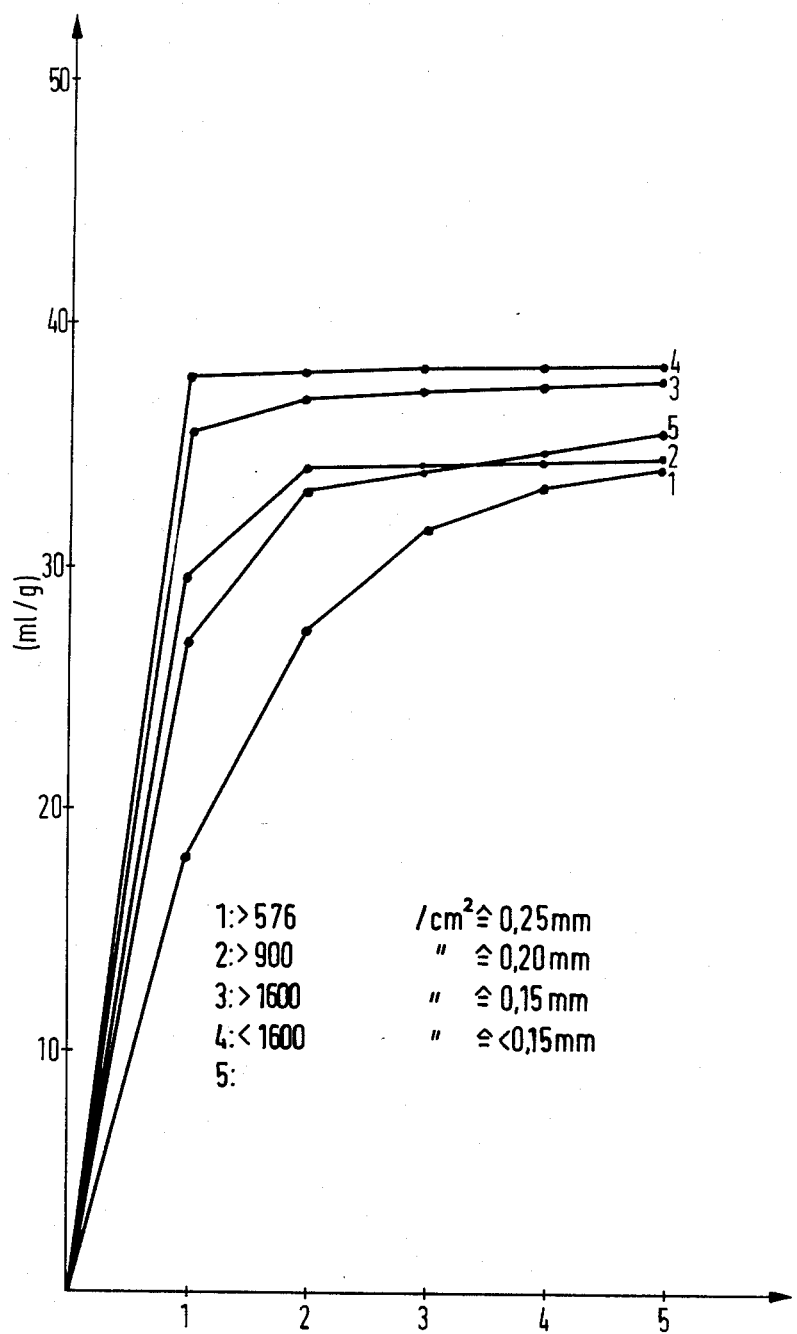

WOUND TREATING AGENT

This is a continuation of application Ser. No. 561,126 filed Dec. 13, 1983, now abandoned which was a continuation of application Ser. No. 304,479 filed Sept. 22, 1981, now abandoned.

This invention relates to wound treating agents in powder form and to a process for the production of such agents.

Wound treating agents in the form of swellable dry powders of organic polymers are already known. One known agent of this kind consists of dry, hydrophilic particles which are a three-dimensional mesh of dextran molecules and, when applied to weeping wounds, they absorb the wound exudate and swell to form a gel-like layer, scab formation hereby also being said to be prevented. Such a wound dressing powder sucks up bacteria due to the capillary forces between the particles. This admittedly results in a sucking up of bacteria from the base of the wound but, on the other hand, it also makes possible the penetration of bacteria from the outside and thus cannot prevent the occurrence of infections. Furthermore, due to its particulate form, it is often difficult completely to remove the agent again from the wounds, although this would be necessary.

Therefore, there is a need for a swellable, granulated wound treating powder which, on the one hand, has a strong absorbing power and, during the absorbing phase, also removes bacteria from the infected base of the wound but which, on the other hand, when, in a swollen state, displays a good adhesion between the swollen particles so that it can easily be removed from the wound as a more or less coherent mass and, at the same time, makes difficult the penetration of bacteria from the outside to the inside.

Initially, it appears to be impossible to combine both apparently mutually opposed properties in one material, namely, fine particularity and high absorbency, on the one hand, and impenetrability for bacteria and high cohesion, on the other hand.

Surprisingly, however, we have found that it is possible to solve this problem and to provide a powdered wound treating agent which combined all these properties, the solution of this problem using, as a starting point, the invention described in Federal Republic of Germany Patent Specification No. 28 49 570.

Federal Republic of Germany Patent Specification No. 28 49 570 discloses a transparent liquid dressing material, which is especially useful for the treatment of wounds, comprising a hydrophilic organic transparent gel in sheet of strip form, which is present as a dry, swellable, clear foil and which can contain buffer substances, active materials conventional in the treatment of wounds, nutrients and/or growth materials and optionally a filamentary or mesh-like strengthening material.

According to a preferred embodiment of the dressing material according to Federal Republic of Germany Patent Specification No. 28 49 570, the gel consists of a gellable polysaccharide and/or protein or polypeptide and a polymer of a hydrophilic acrylic or methacrylic acid derivative, the gel having been produced by polymerisation of the acrylic or methacrylic acid derivative in the presence of the polysaccharide and/or protein or polypeptide.

We have now found that, on the basis of this dry, swellable gel foil, a powdered wound treating agent can be provided which displays surprising and advantageous properties and opens up new possibilities of use.

Thus, according to the present invention, there is provided a wound treating agent in powder form based on a swellable organic polymer, which comprises a cross-linked polymer of a hydrophilic acrylic or methacrylic acid derivative, which polymer is permeated by a gellable polysaccharide and/or protein or polypeptide, the agent being obtainable by the polymerising of a hydrophilic acrylic or methacrylic acid derivative in the presence of a dissolved gellable polysaccharide and/or protein or polypeptide and of a cross-linking agent.

The absorbency of the powder according to the present invention exceeds that of the known powdered wound treating agents and its ability to take up water is several times greater than that of the known powders. Simultaneously, however, the swollen particles "stick" together in such a manner that they not only form a coherent mass which can easily be removed again from the wound but also form a barrier which is impermeable to bacteria and bars the entry of pathogens to the wound.

The hydrophilic acrylic or methacrylic acid derivative, upon which the polymer of the wound treating agent according to the present invention is based, is preferably an amide or ester, the latter containing the residue of an alkanol which possibly still has one or more additional free hydroxyl groups. Agarose is the preferred polysaccharide and gelatine is the preferred protein.

With regard to the composition of the agent, the amount of polymer and of saccharide, protein or polypeptide can vary within wide limits. However, a composition is preferred which contains 50 to 90% by weight of polymerised acrylic or methacrylic acid derivative and 50 to 10% by weight of polysaccharide and/or protein. In the case of this preferred composition, the wound treating agent displays a water takeup of at least 20 ml./g., determined by allowing it to swell for two minutes in salt-free water and preferably in distilled water.

In the case of an especially preferred embodiment, the wound treating agent according to the present invention contains 50 to 70% by weight of cross-linked polyacrylamide and 50 to 30% by weight of gelatine. In the case of this composition, a water take-up of up to 40 ml./g. can be achieved under the above-mentioned conditions.

In contradistinction thereto, the water take-up under the same conditions of a commercially available wound treating agent based on organic polymers is about 5 ml./g.

The cross-linking agent is added in an amount such that the desired swellability is maintained. In general, very good swellabilities are obtained when using about 0.5 to about 5 mol. % of cross-linking agent, referred to the monomer employed, especially favourable results being achieved with 1 to 2 mol % of cross-linking agent. When using acrylamide as the monomer and methylene-bis-acrylamide as the cross-linking agent, this means about 20 to 40 mg. of methylene-bis-acrylamide per gram of acrylamide.

The wound treating powder according to the present invention, when in a swollen state, develops so great an adhesive force that, in most cases, it can be completely removed from the wound by rinsing out. In the swollen state, the gel is sufficiently transparent in order to permit assessment of the colour of the base of the wound through the gel.

The production of the wound treating agent according to the present invention is carried out, as described in Federal Republic of Germany Patent Specification No. 28 49 570, by drying a gel of a particular composition and subsequently comminuting is by grinding or pulverising. In order to obtain a complete and rapid drying, the gel is preferably used in comminuted form, for which purpose there can be used not only the foil form but also a granulation of the gel. In this comminuted form, the gel can also be rapidly washed free of low molecular weight components before drying.

The drying itself can be carried out at any desired temperature between ambient temperature and about 120° C., drying preferably being carried out to a residual water content of less than 10% by weight. However, above 90° C., the drying results in a considerable reduction of the ability of the agent to take up liquid. Especially good results have been obtained by drying at a temperature of from 40° to 80° C. For the drying itself, there otherwise correspondingly apply the statements made in Federal Republic of Germany Patent Specification No. 28 49 570.

The particle size of the powder according to the present invention influences the swelling properties. With decreasing particle size, the rate of liquid take-up increases and, to a lesser extent, also the amount of liquid which can be taken up. In general, a particle size is preferred in which the swelling is substantially concluded between about 0.5 and about 5 minutes, which normally applies in the case of particle sizes of from 0.05 mm. to 0.5 mm. By means of the use of finer or coarser particles, the rate of swelling can, if desired, also be adjusted outside of this range and thereby made greater or smaller. For adjusted properties with regard to the rate of swelling, transparency, cohesion and bacterial impenetrability, mixtures of different particle sizes in the given range are especially preferred.

The wound treating powder according to the present invention can be applied as such to wounds. Alternatively, it is also possible first to convert the powder with a limited amount of liquid into a paste-like consistency and to apply the so obtained gel paste. Syringes are particularly suitable for applying the paste. Application with a syringe containing such a gel paste is very simple in a hospital. The gel is extruded on to and into the wound and left there as long as appears to be expedient. For this purpose, pre-filled sterile ready-to-use syringes can also be employed. As liquids, there can be used solutions which are conventional in the treatment of wounds, especially physiological solutions, water-containing mixtures, for example with mono- or polyhydroxy alcohols, such as glycerol, or other organic liquids, which can contain the substances mentioned in Federal Republic of Germany Patent Specification No. 28 49 570, such as medicaments, nutrients, disinfection agents, growth materials, salts, buffer substances and the agents conventionally used in wound healing, dissolved therein.

The powder according to the present invention can also be used for the qualitative and quantitative determination of low molecular weight substances secreted by wounds. For this purpose, the material taken up is eluted by the methods used in molecular sieve technology, for example by washing out with a salt gradient and analysis of the eluted material. In order to prevent a contamination by undissolved particles from the wounds, portions of the powder can be enclosed in a semi-permeable membrane which is only permeable to dissolved substances or to low molecular weight substances. Depending upon the desired degree of exclusion, for this purpose there can be used conventional dialysis foils or ultrafiltration foils. Bacteria-impermeable fabrics can also be used. Such powder-containing sachets are applied as such to wounds and, after sucking up the secretum, are removed, opened and the powder investigated in the above-described manner.

The following Examples are given for the purpose of illustrating the present invention:-

EXAMPLE 1

Production of a dry gel powder

As described in Example 2 of Federal Republic of Germany Patent Specification No. 27 25 261, starting from 3.2 g. acrylamide, 82 mg. bis-acrylamide and 2 g. agar-agar or agarose, there was produced a gel plate with a thickness of 3 mm. After washing out, it was dried in a drying cabinet for 24 hours at 50° C. The so obtained brittle, dried foil was then ground in a ball mill to an average particle size of less than 0.2 mm. The so obtained product, when swollen in distilled water for 2 minutes, had a water take-up of 40 ml./g.

The drying of the gel plate was repeated, drying being carried out for 30 minutes at a temperature of 100° C. After 2 minutes, the water take-up was 22 ml./g. and after 10 minutes was 28 ml./g.

In a 0.9% aqueous sodium chloride solution, the water take-up after 2 minutes was 22 ml./g. in the case of a powder which had been dried at 50° C.

The determination of the water take-up was carried out by placing 10 ml. distilled water in a 25 ml. glass beaker, weighing it and immersing 100 mg. of dry gel powder in a nylon sieve vessel in the water for 2 minutes. The nylon sieve vessel was then removed and the weight difference of the glass beaker was determined in comparison with the weight before the immersion.

EXAMPLE 2

As described in Example 1 of Federal Republic of Germany Patent Specification No. 27 25 261, starting from 5 g. acrylamide, 5 g. gelatine and 130 mg. N,N'-methylene-bis-acrylamide, there was produced a gel plate with a thickness of 3 mm. After washing out the gel plate, it was dried for 60 hours at 70° C. in a drying cabinet. The so obtained dry foil was ground as described in Example 1. The properties of the product corresponded to those of the powder described in Example 1.

EXAMPLE 3

A gel according to Example 1 was swollen in nutrient broth and inoculated in a test tube with *Serratia marcescens*. As a comparison, the same amount of bacteria was introduced into a test tube with nutrient broth alone. After 2 days incubation, the nutrient broth without gel is non-transparent, reddish and thickly grown with bacteria, whereas the test tube with gel only shows bacterial growth in the uppermost layer. This shows that the powdered gel according to the present invention, when swollen, makes the penetration of bacteria very difficult or impossible.

EXAMPLE 4

A dry gel powder according to the present invention and produced as described in Example 1 was classified with a sieve, four fractions thereby being obtained. Fraction 1 consisted of a portion which did not pass a sieve of 576 apertures/cm$^2$ (about 0.25 mm. aperture width), fraction 2 consisted of particles which passed a 576 aperture sieve but were retained by a 900 aperture/cm$^2$ sieve (about 0.20 mm. aperture width), fraction 3 passed a 900 aperture sieve and was retained by a 1600 aperture sieve (about 0.15 mm. aperture width) and fraction 4 consisted of particles which passed a 1600 aperture sieve.

For each of these four fractions and for the starting mixture, there was determined the water take-up for, in each case, 1 g. of powder in dependence upon the time, the results obtained being summarised in the Figure of the accompanying drawing which shows graphically the water take-up in ml./g., plotted against the time in minutes. Curves 1 to 4 correspond to the water take-up of fractions 1 to 4 and curve 5 shows the water take-up of the non-fractionated mixture. The latter contained 68.1% by weight of fraction 1, 9.4% by weight of fraction 2, 11.4% by weight of fraction 3 and 12.1% by weight of fraction 4. As can be seen from the curves, the rate of water take-up in the case of fraction 4 was, in the initial phase, about twice as great as in the case of fraction 1, whereas the total water take-up after 5 minutes amounts to 38.3 and 34.3 g., respectively.

It will be understood that the specification and examples are illustrative but not limitative of the present invention and that other embodiments within the spirit and scope of the invention will suggest themselves to those skilled in the art.

What is claimed is:

1. Wound treating agent in powder form, comprising (a) 50 to 90 percent by weight of a cross-linked polymer of a hydrophilic acrylic or methacrylic acid derivative, and (b) 10 to 50 percent by weight of at least one gellable material selected from the group consisting of polysaccharides, proteins and polypeptides, wherein said polymer is obtained by polymerizing said hydrophilic acrylic or methacrylic acid derivative in the presence of an aqueous solution of component (b) and about 0.5 to about 5 mol percent of a cross-linking agent per mole of monomer employed.

2. Wound treating agent as claimed in claim 1, obtained by polymerizing acrylamide or methacrylamide in the presence of dissolved agar-agar, agarose or gelatine and as a cross-linking agent, N-N'methylene-bisacrylamide.

3. Wound treating agent as claimed in claim 1 wherein the polysaccharide is agar-agar or agarose and the acrylic or methacrylic acid derivative is acrylamide or methacrylamide.

4. Wound treating agent as claimed in claim 1 wherein the protein is gelatin.

5. Wound treating agent as claimed in claim 1 enveloped in a semi-permeable membrane.

6. Wound treating agent as claimed in claim 1, wherein the agent is in the form of particles the particle size of which is from 0.50 mm. to 0.05 mm.

7. Wound treating agent as claimed in claim 1 wherein said agent contains 50 to 70% by weight of a polymerized acrylic or methacrylic acid derivative and 50 to 30% by weight of a polysaccharide, protein or polypeptide.

8. Wound treating agent as claimed in claim 1 wherein the acrylic or methacrylic acid derivative used is an amide.

9. Wound treating agent as claimed in claim 8 wherein said acrylic acid derivative is acrylamide.

10. Wound treating agent as claimed in claim 8 wherein said methacrylic acid derivative is methacrylamide.

11. Wound treating agent as claimed in claim 1 wherein said agent is in a swollen state.

12. Wound treating agent as claimed in claim 1 further containing medicaments, nutrients, disinfection agents, growth materials, salts and buffer substances.

13. Process for the production of wound treating agent claimed in claim 1, which comprises polymerizing a hydrophilic acrylic or methacrylic acid derivative in an aqueous solution of a gelable member of the group consisting of polysaccharides, proteins and polypeptides, in the presence of a cross-linking agent and of a polymerization initiator, to give a transparent gel, and drying and pulverizing the transparent gel.

14. Process as claimed in claim 13, wherein agarose is used as the polysaccharide.

15. Process according to claim 13, wherein gelatine is used as the protein.

16. Process according to claim 15, wherein the gel is dried at a temperature of from 30° to 90° C.

17. Process according to claim 14, wherein the gel is dried at a temperature of from 40° to 80° C.

18. Process according to claim 17, wherein the gel is dried to a residual water content of less than 10% by weight.

19. Process according to claim 13, wherein the acrylic or methacrylic acid derivative is an amide.

20. Process according to claim 19, wherein the acrylic acid derivative is acrylamide.

21. Process according to claim 19, wherein the methacrylic acid derivative is methacrylamide.

* * * * *